US010492852B2

United States Patent
Soni et al.

(10) Patent No.: US 10,492,852 B2
(45) Date of Patent: Dec. 3, 2019

(54) WIRE GUIDE FOR SURGICAL INSTRUMENTS AND SURGICAL INSTRUMENTS INCLUDING A WIRE GUIDE

(71) Applicant: COVIDIEN LP, Mansfield, MA (US)

(72) Inventors: Purvishkumar H. Soni, Longmont, CO (US); Stephen J. Stamm, Wheat Ridge, CO (US)

(73) Assignee: COVIDIEN LP, Mansfield, MA (US)

( * ) Notice: Subject to any disclaimer, the term of this patent is extended or adjusted under 35 U.S.C. 154(b) by 213 days.

(21) Appl. No.: 15/442,781

(22) Filed: Feb. 27, 2017

(65) Prior Publication Data

US 2018/0243027 A1    Aug. 30, 2018

(51) Int. Cl.
*A61B 18/14* (2006.01)
*A61B 18/00* (2006.01)
*A61B 17/29* (2006.01)

(52) U.S. Cl.
CPC .......... *A61B 18/1445* (2013.01); *A61B 17/29* (2013.01); *A61B 18/1442* (2013.01);
(Continued)

(58) Field of Classification Search
CPC .... A61B 2017/2901; A61B 2017/2902; A61B 2017/2932; A61B 2017/2938; A61B 2017/2944; A61B 17/295; A61B 2018/00053; A61B 2018/00172; A61B 2018/00178; A61B 18/1442; A61B 18/1445; A61B 18/1447; A61B 2018/145;
(Continued)

(56) References Cited

U.S. PATENT DOCUMENTS 5,605,272 A   2/1997  Witt et al.
5,630,782 A   5/1997  Adair
(Continued)

FOREIGN PATENT DOCUMENTS

| AU | 2004216575 A1 | 4/2005 |
| CA | 2844067 A1 | 9/2014 |
| EP | 2319447 A1 | 5/2011 |

OTHER PUBLICATIONS

Partial European Search Report issued in corresponding European application No. 16170578.5 dated Sep. 1, 2016.
(Continued)

*Primary Examiner* — Ronald Hupczey, Jr.
*Assistant Examiner* — Bradford C. Blaise (57) ABSTRACT

A surgical instrument includes a shaft defining a lumen, an end effector assembly disposed at the distal end portion of the shaft, a drive plate, a first electrical wire, and a wire guide. The end effector assembly includes a first electrically-conductive tissue-treating surface. The drive plate extends through the lumen of the shaft and operably engages the end effector assembly such that movement of the drive plate through the lumen of the shaft manipulates the end effector assembly. The first electrical wire also extends through the lumen of the shaft and is configured to supply energy to the first electrically-conductive tissue-treating surface. The wire guide is engaged to a distal portion of the drive plate and is configured to move through the lumen of the shaft in conjunction with the drive plate. The wire guide is also configured to receive the first electrical wire.

14 Claims, 7 Drawing Sheets

(52) U.S. Cl.
CPC ............... *A61B 2017/2901* (2013.01); *A61B 2017/2902* (2013.01); *A61B 2018/00053* (2013.01); *A61B 2018/00178* (2013.01); *A61B 2018/1452* (2013.01); *A61B 2018/1455* (2013.01)

(58) Field of Classification Search
CPC .... A61B 2018/1452; A61B 2018/1455; A61B 2018/1457; A61B 34/30–2034/715
See application file for complete search history.

(56) References Cited

U.S. PATENT DOCUMENTS

| | | | |
|---|---|---|---|
| 5,891,142 | A | 4/1999 | Eggers et al. |
| 5,919,206 | A | 7/1999 | Gengler et al. |
| 5,935,126 | A | 8/1999 | Riza |
| 6,077,287 | A | 6/2000 | Taylor et al. |
| 6,129,740 | A | 10/2000 | Michelson |
| 6,322,579 | B1 | 11/2001 | Muller |
| 6,334,860 | B1 | 1/2002 | Dorn |
| 6,443,968 | B1 | 9/2002 | Holthaus et al. |
| 6,506,208 | B2 | 1/2003 | Hunt et al. |
| 6,706,056 | B2 | 3/2004 | Bacher |
| 6,770,072 | B1 | 8/2004 | Truckai et al. |
| 6,790,217 | B2 | 9/2004 | Schulze et al. |
| 6,887,240 | B1 | 5/2005 | Lands et al. |
| 7,052,496 | B2 | 5/2006 | Yamauchi |
| 7,147,638 | B2 | 12/2006 | Chapman et al. |
| 7,150,097 | B2 | 12/2006 | Sremcich et al. |
| 7,156,846 | B2 | 1/2007 | Dycus et al. |
| 7,384,420 | B2 | 6/2008 | Dycus et al. |
| 7,494,501 | B2 | 2/2009 | Ahlberg et al. |
| 7,549,988 | B2 | 6/2009 | Eberl et al. |
| 7,559,940 | B2 | 7/2009 | McGuire et al. |
| 7,753,909 | B2 | 7/2010 | Chapman et al. |
| 7,758,608 | B2 | 7/2010 | DiCesare et al. |
| 7,766,910 | B2 | 8/2010 | Hixson et al. |
| 7,877,853 | B2 | 2/2011 | Unger et al. |
| 7,922,953 | B2 | 4/2011 | Guerra |
| 8,241,320 | B2 | 8/2012 | Lyons et al. |
| 8,252,021 | B2 | 8/2012 | Boulnois et al. |
| 8,266,783 | B2 | 9/2012 | Brandt et al. |
| 8,388,646 | B2 | 3/2013 | Chojin |
| 8,394,094 | B2 | 3/2013 | Edwards et al. |
| 8,409,244 | B2 | 4/2013 | Hinman et al. |
| 8,545,534 | B2 | 10/2013 | Ahlberg et al. |
| 8,551,090 | B2 | 10/2013 | Sutter et al. |
| 8,728,118 | B2 | 5/2014 | Hinman et al. |
| 8,740,933 | B2 | 6/2014 | Anderson |
| 8,789,741 | B2 | 7/2014 | Baxter, III et al. |
| 8,814,856 | B2 | 8/2014 | Elmouelhi et al. |
| 8,858,553 | B2 | 10/2014 | Chojin |
| 2005/0090837 | A1 | 4/2005 | Sixto et al. |
| 2007/0078459 | A1 | 4/2007 | Johnson et al. |
| 2010/0063525 | A1 | 3/2010 | Beaupre et al. |
| 2011/0009864 | A1* | 1/2011 | Bucciaglia ......... A61B 17/2909 606/52 |
| 2011/0270251 | A1 | 11/2011 | Horner et al. |
| 2013/0296856 | A1* | 11/2013 | Unger ................ A61B 17/2816 606/52 |
| 2014/0025073 | A1 | 1/2014 | Twomey et al. |
| 2016/0338718 | A1 | 11/2016 | Allen, IV et al. |
| 2016/0338719 | A1 | 11/2016 | Allen, IV et al. |
| 2016/0338762 | A1 | 11/2016 | Krastins et al. |
| 2016/0338763 | A1 | 11/2016 | Allen, IV et al. |
| 2016/0338764 | A1 | 11/2016 | Krastins et al. |

OTHER PUBLICATIONS

Extended European search report issued in corresponding application No. 16170578.5 dated Dec. 5, 2016.

* cited by examiner

WIRE GUIDE FOR SURGICAL INSTRUMENTS AND SURGICAL INSTRUMENTS INCLUDING A WIRE GUIDE

BACKGROUND

Technical Field

The present disclosure relates to surgical instruments, more particularly, to a wire guide for surgical instruments, the wire guide configured to guide one or more wires from a shaft of the surgical instrument into an end effector of the surgical instrument.

Background of Related Art

Many surgical instruments communicate energy to an end effector assembly for treating tissue. For example, energy-based surgical forceps utilize both mechanical clamping action and energy to treat, e.g., coagulate, cauterize, and/or seal, tissue.

Currently, energy-based surgical forceps are designed to include one or more hollow or semi-hollow housings, which typically house and/or operably couple to a shaft supporting an end effector assembly, a handle assembly, a trigger assembly, a drive assembly, an energy activation assembly, and one or more electrical wires which extend through the housing and shaft to supply energy to the end effector assembly for treating tissue therewith. It is desirable to protect the electrical wires from potential damage from, as well as from interference with, the other components of the forceps.

SUMMARY

A surgical instrument provided in accordance with aspects of the present disclosure includes a shaft defining a lumen therethrough, an end effector assembly disposed at a distal portion of the shaft, a drive plate, a first electrical wire, and a wire guide. The drive plate extends through the lumen of shaft. The drive plate is also operably engaged with the end effector assembly such that the movement of the drive plate through the lumen of the shaft manipulates the end effector assembly. The end effector assembly includes a first electrically-conductive tissue-treating surface. The first electrical wire extends through the lumen of the shaft and is configured to supply energy to the first electrically-conductive tissue-treating surface. The wire guide is engaged to a distal portion of the drive plate and is configured to move through the lumen of the shaft in conjunction with the drive plate and to receive the first electrical wire.

In an aspect of the present disclosure, the wire guide includes a first guiding support configured to receive the first electrical wire. The wire guide also includes a plate and a first leg extending from the plate. The first guiding support is disposed on the first leg of the wire guide. Further, the first guiding support defines a U-shaped channel configured to receive the first electrical wire.

In an aspect of the present disclosure, the surgical instrument further includes a second electrical wire extending through the lumen of the shaft. The second electrical wire is configured to supply energy to a second electrically-conductive tissue treating surface. The wire guide is configured to receive the second electrical wire. Additionally, the wire guide includes a second guiding support configured to receive the second electrical wire. Further, the wire guide includes a plate and a second leg extending from the plate. The second guiding support is disposed on the second leg of the wire guide and defines a U-shaped channel configured to receive the second electrical wire.

In an aspect of the present disclosure, the movement of the drive plate through the lumen of the shaft moves the wire guide relative to the first electrical wire.

Another surgical instrument provided in accordance with aspects of the present disclosure includes a shaft defining a lumen, an end effector assembly disposed at a distal end portion of the shaft, a drive plate, a first electrical wire, and a wire guide. The drive plate extends through the lumen of the shaft and is operably engaged with the end effector assembly such that movement of the drive plate through the lumen of the shaft manipulates the end effector assembly. The first electrical wire also extend through the lumen of the shaft and into electrical communication with the end effector assembly. The wire guide includes a body and a first guiding support disposed on the body. Additionally, the wire guide is engaged to a distal portion of the drive plate such that the wire guide is moved through the lumen of the shaft in conjunction with the movement of the drive plate therethrough. The first guiding support is configured to receive the first electrical wire.

In an aspect of the present disclosure, the surgical instrument further includes a second electrical wire extending through the shaft and into electrical communication with the end effector assembly. The wire guide is configured to receive the second electrical wire. Additionally, the wire guide includes a second guiding support that is configured to receive the second electrical wire. The first guiding support and the second guiding support are positioned substantially parallel to one another. Also, the first guiding support and the second guiding support are disposed on opposing sides of the wire guide.

In an aspect of the present disclosure, the movement of the drive plate through the lumen of the shaft moves the wire guide relative to the first electrical wire.

Another surgical instrument provided in accordance with aspects of the present disclosure includes a shaft defining a lumen therethrough, an end effector assembly disposed at a distal end portion of the shaft, a drive plate, a first electrical wire, a second electrical wire, and a wire guide. The end effector assembly includes first and second jaw members each defining an electrically-conductive tissue-treating surface. At least one of the first or second jaw members is movable relative to the other to transition the first and second jaw members between a spaced-apart position and an approximated position for grasping tissue between the electrically-conductive tissue-treating surfaces. The drive plate extends through the lumen of the shaft and is operably engaged with the first and/or second jaw member such that movement of the drive plate through the lumen of the shaft moves the first and second jaw members between the spaced-apart and approximated positions. The first electrical wire also extends through the lumen of the shaft and into electrical communication with the electrically-conductive tissue-treating surface of the first jaw member. The second electrical wire likewise extends through the lumen of the shaft and into electrical communication with the electrically-conductive tissue-treating surface of the second jaw member. The wire guide includes a body, a first guiding support disposed on the body, and a second guiding support disposed on the body. The wire guide is engaged to a distal portion of the drive plate. The first guiding support is configured to receive the first electrical wire and the second guiding support is configured to receive the second electrical wire.

In an aspect of the present disclosure, the first guiding support is disposed on a first side of the body of the wire guide and the second guiding support is disposed on a second, opposite side of the body of the wire guide. The movement of the drive plate through the lumen of the shaft moves the wire guide relative to the first and second electrical wires.

BRIEF DESCRIPTION OF THE DRAWINGS

Various aspects and features of the present disclosure are described herein with reference to the drawings wherein.

DETAILED DESCRIPTION

As used herein, the term "distal" refers to the portion that is being described which is further from a user, while the term "proximal" refers to the portion that is being described which is closer to a user. Additionally, as used herein, the term "substantially parallel" refers to a position within 10 degrees of parallel. Further, to the extent consistent, any of the aspects described herein may be used in conjunction with any or all of the other aspects described herein.

Figure 1:
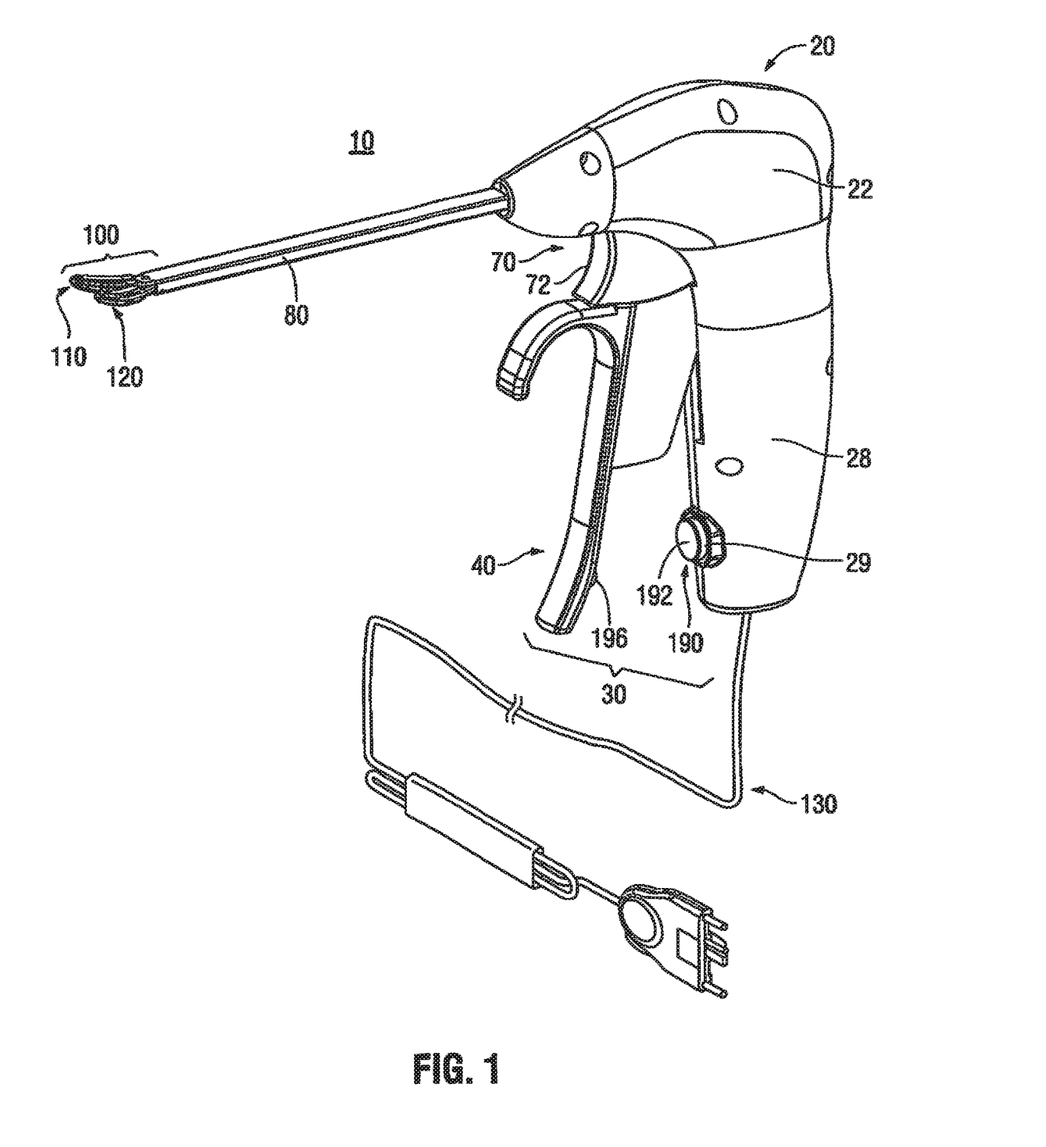
FIG. 1 is a front, perspective view of a surgical instrument provided in accordance with an embodiment of the present disclosure with jaw members of the end effector assembly of the surgical instrument disposed in a spaced-apart position.

Referring generally to FIG. 1, a surgical instrument provided in accordance with an embodiment of the present disclosure is shown generally identified by reference numeral 10. Instrument 10, as described below, is configured for grasping, treating, and/or dissecting tissue. For the purposes herein, instrument 10 is generally described. Additional features contemplated for use with instrument 10 are detailed in U.S. patent application Ser. Nos. 14/719,422, 14/719,434, 14/719,452, 14/719,464, and 14/719,475, each of which was filed on May 22, 2015, and is incorporated herein by reference in its entirety.

Figure 2:
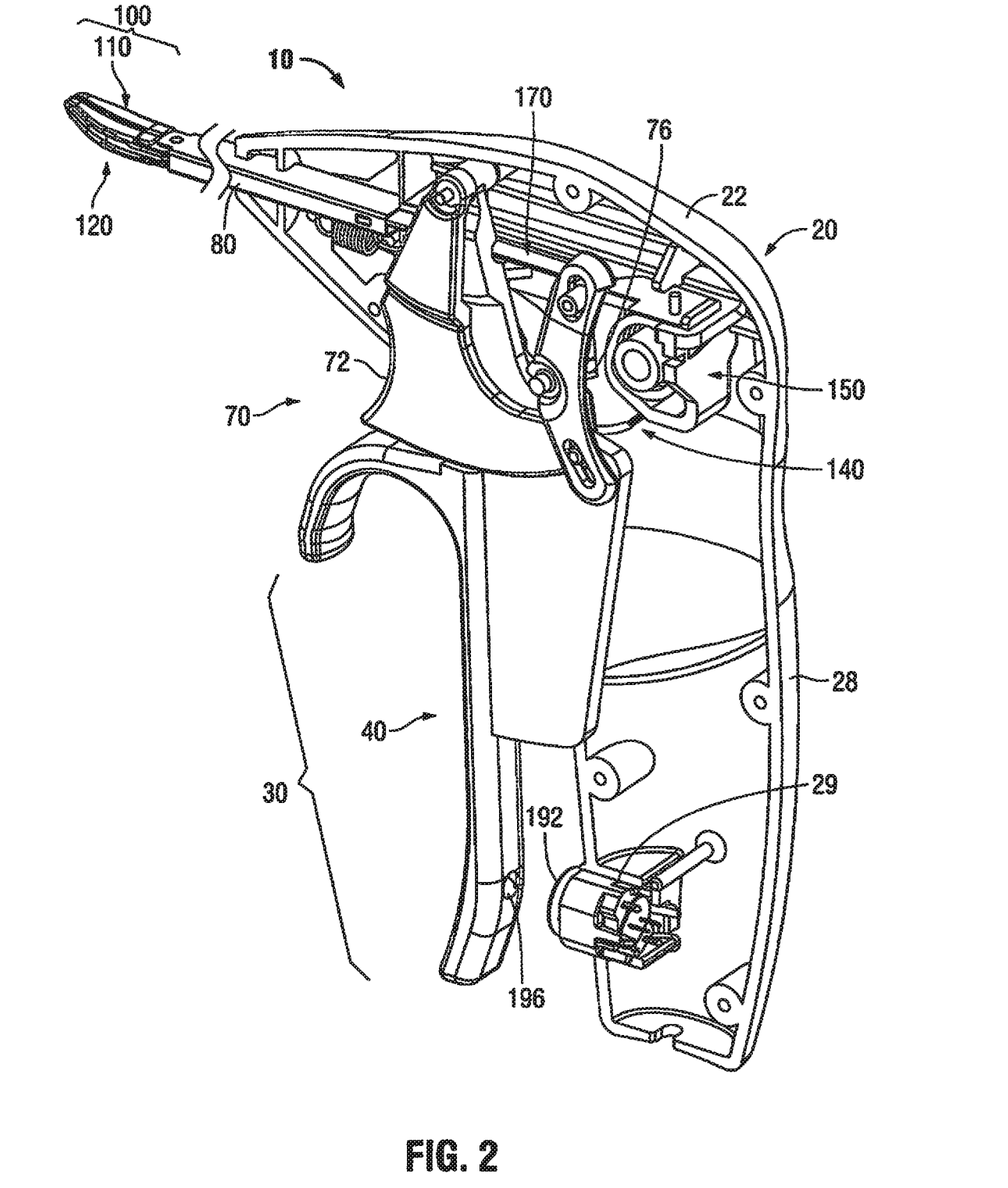
FIG. 2 is a rear, perspective view of the surgical instrument of FIG. 1 with the jaw members disposed in an approximated position and a portion of a housing of the surgical instrument removed to illustrate the internal components therein.
Figure 3:
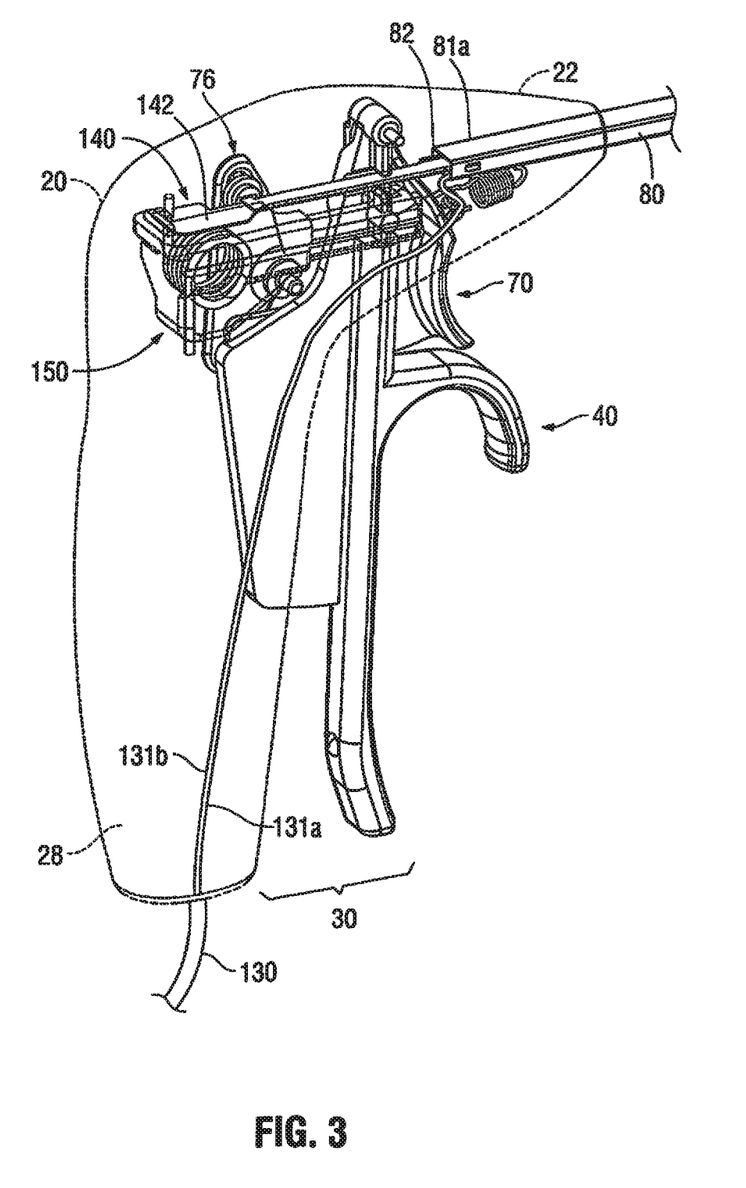
FIG. 3 is a rear, perspective view of the various components disposed within or coupled to the housing of the surgical instrument of FIG. 1.

With reference to FIGS. 1-3, instrument 10 generally includes a housing 20, a handle assembly 30, a trigger assembly 70, a shaft 80, a wire guide 200 (FIGS. 4 and 5), an end effector assembly 100, a drive assembly 140, a knife assembly 170, and an energy activation assembly 190.

The housing 20 houses the internal working components of instrument 10 and is formed from first and second housing components configured to engage one another via a plurality of pin-aperture engagements spaced around an outer perimeter of the housing 20, although other suitable engagements, e.g., screws, snap-fit connections, adhesion, ultrasonic welding, etc., are also contemplated, as are different formations of housing 20. Housing 20 defines a pistol-style configuration having a longitudinally-extending barrel portion 22 and a fixed handle portion 28 that extends from barrel portion 22 in generally perpendicular orientation relative thereto.

Shaft 80 extends distally from housing 20 and defines a proximal end portion 81a, a distal end portion 81b, and a lumen 82 extending longitudinally therethrough. Proximal end portion 81a of shaft 80 is engaged to housing 20, while distal end portion 81b of shaft 80 supports end effector assembly 100. Lumen 82 provides a pathway for drive assembly 140, first electrical wire 131a, and second electrical wire 131b from housing 20 to end effector assembly 100.

Figure 4:
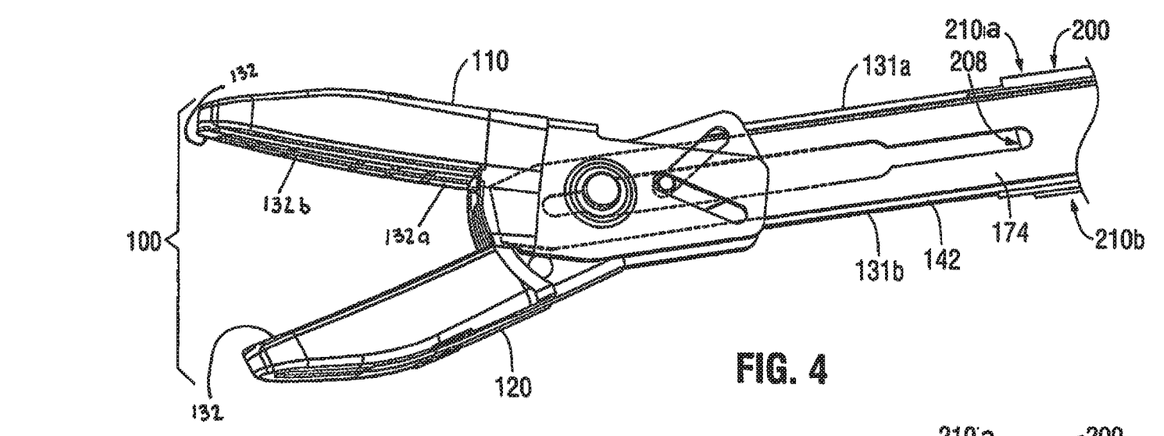
FIG. 4 is a perspective view of a distal end portion of the surgical instrument of FIG. 1 with the shaft removed and the jaw members disposed in the spaced-apart position.
Figure 5:
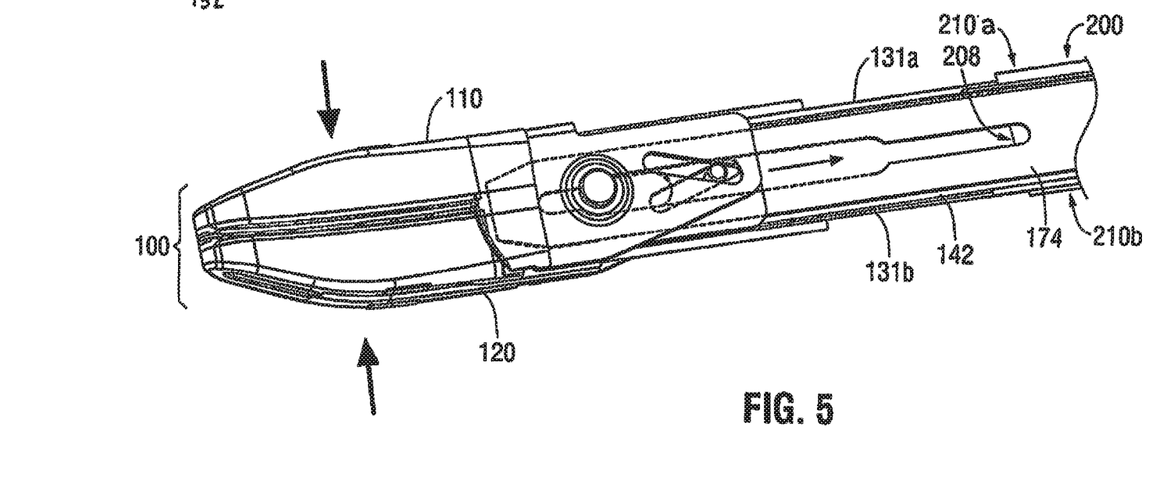
FIG. 5 is a perspective view of a distal end portion of the surgical instrument of FIG. 1 with the shaft removed and the jaw members disposed in the spaced-apart position, illustrating a wire guide in accordance with the present disclosure routing wires along a drive plate to the jaw members.

Continuing with reference to FIGS. 1-3, handle assembly 30 includes a movable handle 40 that is movable relative to fixed handle portion 28 of housing 20 between an initial position, a compressed position, and an activated position to impart movement of jaw members 110, 120 of end effector assembly 100 between a spaced-apart position (FIG. 4) and an approximated position (FIG. 5) for grasping tissue therebetween and for initiating the supply of energy to end effector assembly 100 for treating grasped tissue. Drive assembly 140 operably couples handle assembly 30 with end effector assembly 100 to enable selective manipulation of jaw members 110, 120 of end effector assembly 100 via actuation of movable handle 40. More specifically, with additional reference to FIGS. 4 and 5, drive assembly 140 includes a drive plate 142 and a slider assembly 150. Drive plate 142 extends distally from housing 20 and through shaft 80 to operably engage end effector assembly 100, e.g., via a cam-slot arrangement, while slider assembly 150 operably couples drive plate 142 and movable handle 40 with one another such that actuation of movable handle 40 translates drive plate 142 through shaft 80 and relative to end effector assembly 100 to pivot jaw members 110, 120 of end effector assembly 100 between the spaced-apart and approximated positions (FIGS. 4 and 5, respectively). Drive plate 142 is oriented similarly to shaft 80, such that the width of drive plate 142 extends along the width dimension of shaft 80, although other configurations of shaft 80 and drive plate 142 may alternatively be provided. Drive plate 142 also supports a wire guide 200 configured to move with drive plate 142 through shaft 80 and to guide electrical wires 131a, 131b through shaft 80 to end effector assembly 100, as detailed below.

Knife assembly 170 is operably coupled with trigger assembly 70 to enable selective translation of a knife blade 174 (FIGS. 4 and 5) of knife assembly 170 relative to end effector assembly 100 via actuation of trigger assembly 70. Trigger assembly 70, more specifically, includes a trigger 72 and a linkage 76. Linkage 76 serves to operably couple trigger 72 with knife assembly 170 such that pivoting of trigger 72 from the un-actuated position to the actuated position advances knife blade 174 between jaw members 110, 120 of end effector assembly 100 to cut tissue grasped therebetween.

Energy activation assembly 190 includes a depressible button 192 that is mechanically coupled to a switch 194 mounted within a bay 29 defined within fixed handle portion 28 of housing 20 and is engagable by a button activation post 196 extending proximally from a proximal side of movable handle 40 upon movement of movable handle 40 to the activated position. Switch 194 is configured to electrically communicate with end effector assembly 100 and a generator (not shown) via the first and second electrical wires 131a, 131b extending through housing 20 and shaft 80 to enable energy to be supplied from the generator to end effector assembly 100 upon activation of switch 194.

Continuing with reference to FIGS. 1-5, as mentioned above, end effector assembly 100 is operably supported at the distal end portion 81b of shaft 80. End effector assembly 100 includes opposing jaw members 110, 120 pivotally coupled to one another and movable relative to one another and shaft 80 between a spaced-apart position and an approximated position for grasping tissue therebetween, although unilateral configurations are also contemplated. Each jaw member 110, 120 includes an electrically-conductive plate 132. The electrically-conductive plate 132 of each jaw member 110, 120 defines a generally planar tissue-contacting surface 132a and an elongated knife slot 132b extending through and defined within the respective tissue-contacting surface 132a.

Figure 6A:
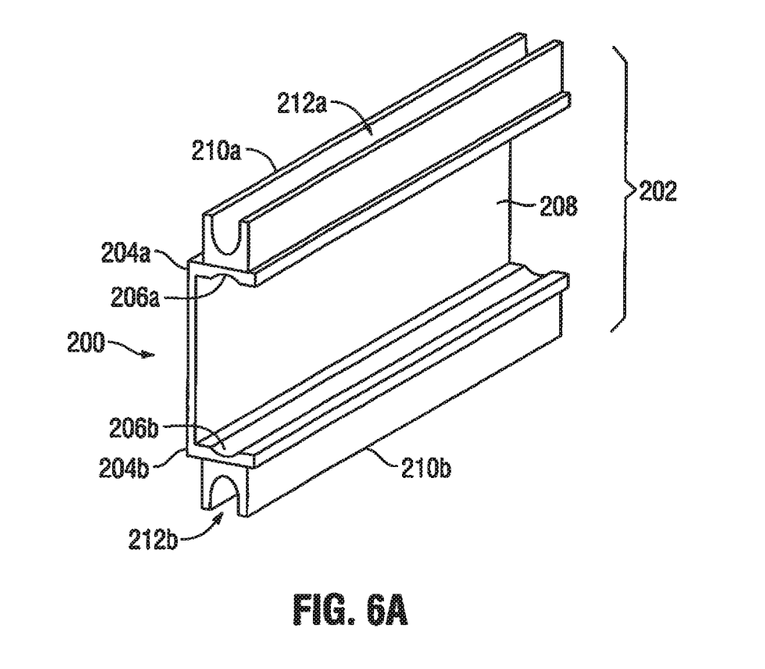
FIG. 6A is a perspective view of the wire guide of FIGS. 4 and 5.
Figure 6B:
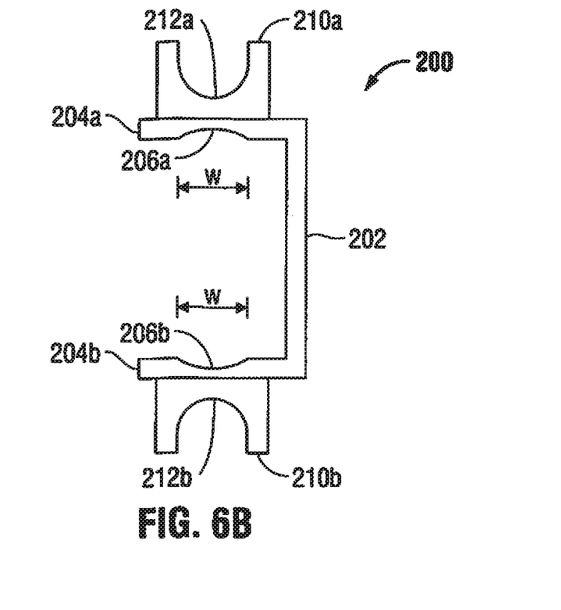
FIG. 6B is a transverse, end view of the wire guide of FIGS. 4 and 5.
Figure 6C:
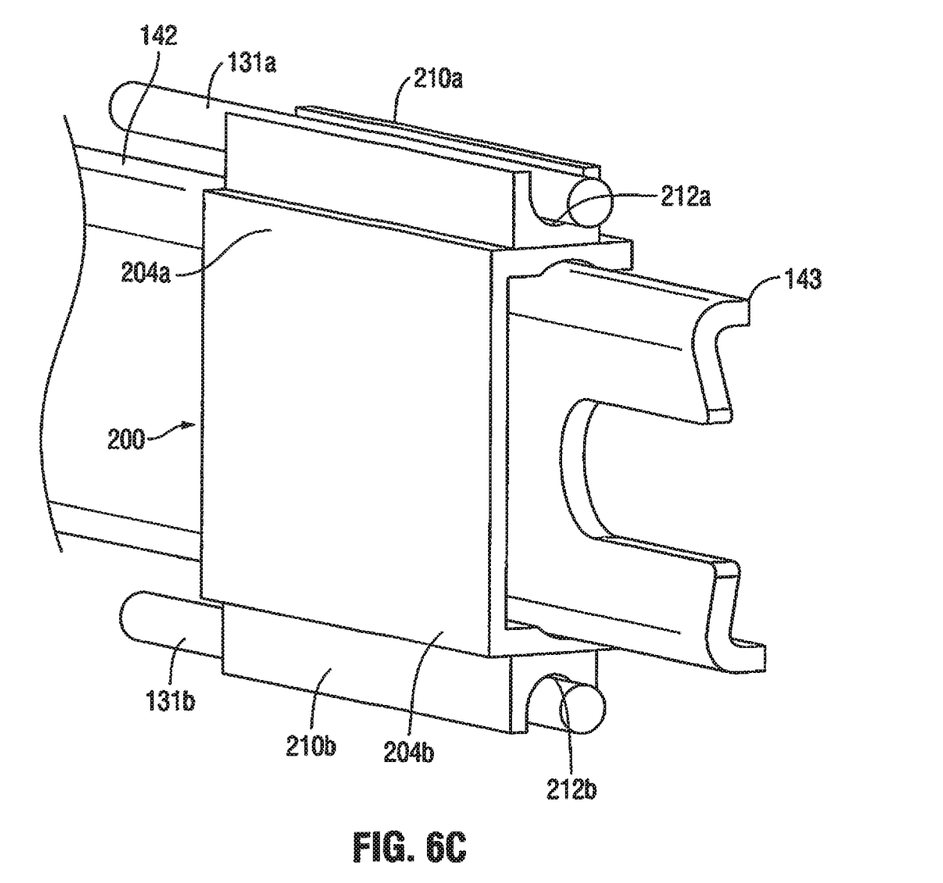
FIG. 6C is a perspective view of the wire guide of FIGS. 4 and 5 engaged about the drive plate of FIGS. 4 and 5.

With reference to FIGS. 6A-6C, wire guide 200 includes a body 202, a first guiding support 210a, and a second guiding support 210b. The body 202 includes a first leg 204a, a second leg 204b, and a plate 208 interconnecting first and second legs 204a, 204b. The plate 208 is configured similarly to a distal portion 143 of the drive plate 142 and may include engagement and/or retention features configured to secure plate 208 in position relative to drive plate 142. Plate 208 and drive plate 142 may sit flush with one another or may define a gap therebetween to permit passage of knife blade 174 (FIGS. 4 and 5) therebetween. In such embodiments, plate 208 thus also functions as a knife guide to guide translation of knife blade 174 (FIGS. 4 and 5).

The plate 208 extends generally perpendicularly between the first leg 204a and the second leg 204b such that the first and second legs 204a, 204b are positioned substantially parallel to one another. Substantially parallel is defined here in as being within 10 degrees of parallel. In one embodiment, the first leg 204a, the second leg 204b, and the plate 208 are interconnected to form a C-shape arrangement. In this embodiment, the first and second legs 204a, 204b are positioned to rest upon opposites narrow sides of the distal portion 143 of the drive plate 142, while plate 208 extends along one of the wider sides of the distal portion 143 of the drive plate 142. Each of the first and second legs 204a, 204b includes a track 206a, 206b, respectively, disposed on an inwardly-facing surface thereof. Each of the tracks 206a, 206b has a width "w," which may have a generally rectangular transverse cross-sectional profile. Width "w" may be sufficiently sized to allow the positioning of the narrow sides of distal portion 143 of the drive plate 142 within tracks 206a, 206b. Thus, the width "w" may be slightly larger than the width of the narrow sides of the distal portion 143 of the drive plate 142.

As mentioned above, the wire guide 200 includes a first guiding support 210a and a second guiding support 210b. Both the first and second guiding supports 210a, 210b are configured to guide the first electrical wire 131a and the second electrical wire 131b, respectively, from the distal portion 143 of the drive plate 142 to the end effector assembly 100. First and second guiding supports 210a, 210b may be structurally similar to one another. Thus, common features to both first and second guiding supports 210a, 210b may not be described and/or illustrated with respect to each of first and second guiding supports 210a, 210b.

Each of the first and second guiding supports 210a, 210b defines a U-shape channel 212a, 212b. Although channels 212a and 212b are shown as a radiused U-shape, it is contemplated that other cross-sectional shapes may be used, for example, a V-shaped cross-section, squared U-shaped cross-section, etc. The U-shape channels 212a, 212b are configured to receive the first and second electrical wires 131a, 131b, and in embodiments have a shape corresponding to the shape of electrical wires 131a, 131b. First and second guiding supports 210a, 210b are positioned on an outwardly-facing side of the wire guide 200, opposite the respective tracks 206a, 206b. In embodiments, the first guiding support 210a is integrally formed with the first leg 204a. In other embodiments, the first guiding support 210a is a separate structure connected to the first leg 204a. In such embodiments, the first guiding support 210a may be connected to the wire guide 200 by any appropriate method, e.g., welding. Both the first and second guiding supports 210a, 210 b may extend the entire length of the wire guide 200, or portions thereof.

The first and second guiding supports 210a, 210b separate and guide the respective first and second electrical wires 131a, 131b along the drive plate 142 to the electrically-conductive plate 132 of each jaw member 110, 120 for electrical connection therewith. Wires 131a, 131b are inserted through U-shaped channels 212a, 212b, respectively, and may be seated therein while still enabling longitudinal sliding of wires 131a, 131b relative to wire guide 200 as drive plate 142 is translated to move jaw members 110, 120. In embodiments, wires 131a, 131b flex guiding supports 210a, 210b to permit passage of wires 131a, 131b, into U-shaped channels 212a, 212b, respectively. Once wires 131a, 131b are positioned within U-shaped channels 212a, 212b, guiding supports 210a, 210b are returned to their at-rest positions securing wires 131a, 131b within U-shaped channels 212a, 212b, respectively, and inhibiting backing-out of wires 131a, 131b, while still enabling longitudinal sliding of wires 131a, 131b relative to wire guide 200 as drive plate 142 is translated to move jaw members 110, 120. Wire guide 200 ensures that the first and second electrical wires 131a, 131b are appropriately positioned so as not to interfere with movement of the jaw members 110, 120 between the spaced-apart and approximated positions (FIGS. 4 and 5, respectively).

Figure 7A:
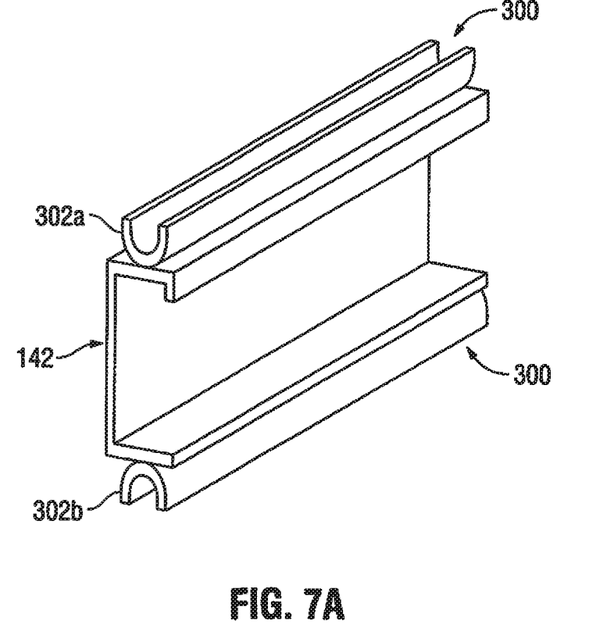
FIG. 7A is a perspective view of another embodiment of a wire guide in accordance with the present disclosure disposed on the drive plate of the surgical instrument of FIGS. 4 and 5.
Figure 7B:
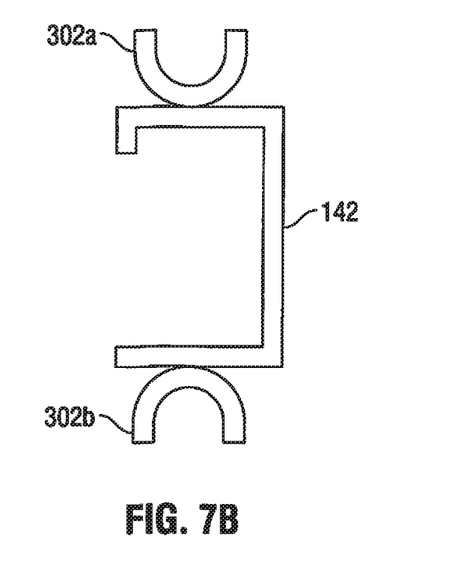
FIG. 7B is an end view of the wire guide of FIG. 7A disposed on the drive plate of the drive assembly of the surgical instrument of FIG. 5.

With reference to FIGS. 7A and 7B, another embodiment of a wire guide 300 is illustrated. Wire guide 300 includes a first guiding support 302a and a second guiding support 302b. First and second guiding supports 302a, 302b are similar to the first and second guiding supports 210a, 210b (FIGS. 6A-6C) and, thus, common features may not be explicitly described below. Each the first and second guiding supports 302a, 302b is directly connected to or integrally formed on an outwardly-facing portion of one of the narrow sides of the distal portion 143 of the drive plate 142. Thus, wire guide 300 differs from wire guide 200 (FIGS. 6A-6C) in that wire guide 300 includes guide supports 302a, 302b disposed directly on drive plate 142 rather than including a plate configured to engage drive plate 142 as with wire guide 200 (FIGS. 6A-6C).

Referring generally to FIGS. 1-7B, as mentioned above, wire guides 200, 300 are configured to guide first electrical wire 131a and second electrical wire 131b from the drive plate 142 to the end effector assembly 100 in order to operably couple a generator, energy activation assembly 190, and end effector assembly 100. An electrosurgical cable 130 (FIG. 3) houses a portion of the first and second electrical wires 131*a*, 131*b* and extends from the generator into fixed handle portion 28 of housing 20. The electrosurgical cable 130 and first and second electrical wires 131*a*, 131*b* enter the housing 20 and extend through the housing 20. Each of the first and second electrical wires 131*a*, 131*b* enters the proximal end portion 81*a* of the shaft 80, extends the entire length of the shaft 80, is secured by the wire guides 200, 300, and ultimately is connected to one of the jaw members 110, 120 of the end effector assembly 100. As such, wires 131*a*, 131*b* extend through shaft 80 along the drive plate 142. Wire guides 200, 300 help ensure that first and second electrical wires 131*a*, 131*b* are maintained in position through shaft 80, remain undamaged, do not interfere with any of the other components extending through shaft 80, and are properly routed to electrically connect with the electrically-conductive plates 132 of jaw members 110, 120, respectively.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a shaft defining a lumen therethrough;
   an end effector assembly disposed at a distal end portion of the shaft, the end effector assembly including a first electrically-conductive tissue-treating surface;
   a drive plate extending through the lumen of the shaft and operably engaged with the end effector assembly such that movement of the drive plate through the lumen of the shaft manipulates the end effector assembly;
   a first electrical wire extending through the lumen of the shaft and configured to supply energy to the first electrically-conductive tissue-treating surface; and
   a wire guide engaged to a distal portion of the drive plate, the wire guide configured to move through the lumen of the shaft in conjunction with the drive plate and to receive the first electrical wire, wherein the wire guide is non-pivotable relative to the shaft.

2. The surgical instrument of claim 1, wherein the wire guide includes a first guiding support configured to receive the first electrical wire.

3. The surgical instrument of claim 2, wherein the wire guide includes a plate and a first leg extending from the plate, the first guiding support disposed on the first leg of the wire guide.

4. The surgical instrument of claim 2, wherein the first guiding support defines a U-shaped channel configured to receive the first electrical wire.

5. The surgical instrument of claim 1, further including a second electrical wire extending through the lumen of the shaft and configured to supply energy to a second electrically-conductive tissue-treating surface, wherein the wire guide is configured to receive the second electrical wire.

6. The surgical instrument of claim 5, wherein the wire guide includes a second guiding support configured to receive the second electrical wire.

7. The surgical instrument of claim 6, wherein the wire guide includes a plate and a second leg extending from the plate, the second guiding support disposed on the second leg of the wire guide.

8. The surgical instrument of claim 6, wherein the second guiding support defines a U-shaped channel configured to receive the second electrical wire.

9. The surgical instrument of claim 1, wherein, upon movement of the drive plate through the lumen of the shaft, the wire guide is moved relative to the first electrical wire.

10. A surgical instrument, comprising:
    a shaft defining a lumen therethrough;
    an end effector assembly disposed at a distal end portion of the shaft;
    a drive plate extending through the lumen of the shaft and operably engaged with the end effector assembly such that movement of the drive plate through the lumen of the shaft manipulates the end effector assembly;
    a first electrical wire extending through the lumen of the shaft and into electrical communication with the end effector assembly; and
    a wire guide engaged to a distal portion of the drive plate such that the wire guide is moved through the lumen of the shaft in conjunction with movement of the drive plate therethrough, the wire guide including:
    a body;
    a first guiding support disposed on the body and facing a first direction, the first guiding support configured to receive the first electrical wire; and
    a second guiding support disposed on the body and facing a second direction, the second direction being different from the first direction, the second guiding support configured to receive a second wire.

11. The surgical instrument of claim 10, wherein the first guiding support and the second guiding support are positioned substantially parallel to one another.

12. The surgical instrument of claim 11, wherein the first guiding support and the second guiding support are disposed on opposing sides of the wire guide.

13. The surgical instrument of claim 10, wherein, upon movement of the drive plate through the lumen of the shaft, the wire guide is moved relative to the first electrical wire.

14. The surgical instrument of claim 10, wherein:
    the first guiding support defines a U-shaped channel,
    the second guiding support defines a U-shaped channel, and
    the first direction is opposite from the second direction.

* * * * *